United States Patent
Dua et al.

(10) Patent No.: US 6,746,489 B2
(45) Date of Patent: Jun. 8, 2004

(54) PROSTHESIS HAVING A SLEEVE VALVE

(75) Inventors: Kulwinder S. Dua, Brookfield, WI (US); Scott T. Moore, Rural Hill, NC (US); John A. Karpiel, Winston-Salem, NC (US)

(73) Assignee: Wilson-Cook Medical Incorporated, Winston-Salem, NC (US)

( * ) Notice: Subject to any disclaimer, the term of this patent is extended or adjusted under 35 U.S.C. 154(b) by 0 days.

(21) Appl. No.: 09/876,520

(22) Filed: Jun. 7, 2001

(65) Prior Publication Data

US 2002/0032487 A1 Mar. 14, 2002

Related U.S. Application Data

(63) Continuation-in-part of application No. 09/386,173, filed on Aug. 31, 1999, now Pat. No. 6,302,917.
(60) Provisional application No. 60/211,753, filed on Jun. 14, 2000, and provisional application No. 60/098,542, filed on Aug. 31, 1998.

(51) Int. Cl.$^7$ .................................................. A61F 2/36
(52) U.S. Cl. .................................................... 623/23.68
(58) Field of Search ................................. 623/1.24, 1.25, 623/11.11, 23.64, 23.65, 23.66, 23.67, 23.68, 23.69, 23.7; 604/8, 9; 606/108, 191, 194

(56) References Cited

U.S. PATENT DOCUMENTS

| | | | |
|---|---|---|---|
| 3,868,956 | A | 3/1975 | Alfidi et al. |
| 3,890,977 | A | 6/1975 | Wilson |
| 3,996,938 | A | 12/1976 | Clark, III |
| 4,149,911 | A | 4/1979 | Clabburn |
| 4,271,827 | A | 6/1981 | Angelchik |
| 4,306,318 | A | 12/1981 | Mano et al. |
| 4,425,908 | A | 1/1984 | Simon |
| 4,445,896 | A | 5/1984 | Gianturco |
| 4,494,531 | A | 1/1985 | Gianturco |
| 4,503,569 | A | 3/1985 | Dotter |
| 4,512,338 | A | 4/1985 | Balko et al. |

(List continued on next page.)

FOREIGN PATENT DOCUMENTS

| | | |
|---|---|---|
| DE | 8905127 | 8/1989 |
| EP | 0275535 | 7/1988 |
| EP | 0480667 | 4/1992 |
| EP | 0808614 | 11/1997 |

(List continued on next page.)

OTHER PUBLICATIONS

Gray, Henry, Grays Anatomy, 874 (Barnes & Noble Books, 15 ed.).
Palliation of Gastroesophageal Carcinoma With Endoscopic Insertion of a new Antireflux Prosthesis, Jose Valbuena, M.D. Gastrointestinal Endoscopy, vol. 30, No. 4, 1984.

(List continued on next page.)

*Primary Examiner*—Corrine McDermott
*Assistant Examiner*—William H. Matthews
(74) *Attorney, Agent, or Firm*—Brinks Hofer Gilson & Lione

(57) ABSTRACT

Disclosed is a pressure sensitive prosthesis (10) that includes a tubular member (11) having a passageway (12) extending therethrough and a sleeve (13) attached about one end of the tubular member. The sleeve functions as a one-way valve to permit fluid flowing through the sleeve lumen (15) in a first direction (17) and under a first pressure, while collapsing in response to fluid flowing in a second direction 18 where the pressure that exceeds that of the first direction or pressure. One aspect of the invention includes an esophageal antireflux expandable prosthesis wherein the sleeve is adapted to invert back through the tubular stent frame to permit belching or vomiting (fluid or materials under a third, significantly higher pressure). Another aspect of the invention includes a tubular drainage stent (60), such as a biliary or urethral stent in which the sleeve opens to permit passage of fluids, then collapses to prevent retrograde flow.

5 Claims, 9 Drawing Sheets

U.S. PATENT DOCUMENTS

| | | |
|---|---|---|
| 4,553,545 A | 11/1985 | Maass et al. |
| 4,560,374 A | 12/1985 | Hammerslag |
| 4,572,186 A | 2/1986 | Gould et al. |
| 4,580,568 A | 4/1986 | Gianturco |
| 4,636,313 A | 1/1987 | Vaillancourt |
| 4,649,922 A | 3/1987 | Wiktor |
| 4,655,771 A | 4/1987 | Wallsten |
| 4,657,530 A | 4/1987 | Buchwald et al. |
| 4,665,918 A | 5/1987 | Garza et al. |
| 4,681,110 A | 7/1987 | Wiktor |
| 4,687,468 A | 8/1987 | Gianturco |
| 4,699,611 A | 10/1987 | Bowden |
| 4,716,900 A | 1/1988 | Ravo et al. |
| 4,719,916 A | 1/1988 | Ravo |
| 4,723,549 A | 2/1988 | Wholey et al. |
| 4,729,766 A | 3/1988 | Bergentz et al. |
| 4,732,152 A | 3/1988 | Wallsten et al. |
| 4,733,665 A | 3/1988 | Palmaz |
| 4,739,762 A | 4/1988 | Palmaz |
| 4,762,128 A | 8/1988 | Rosenbluth |
| 4,768,507 A | 9/1988 | Fichell et al. |
| 4,776,337 A | 10/1988 | Palmaz |
| 4,793,348 A | 12/1988 | Palmaz |
| 4,794,928 A | 1/1989 | Kletschka |
| 4,800,882 A | 1/1989 | Gianturco |
| 4,820,298 A | 4/1989 | Leveen et al. |
| 4,825,861 A | 5/1989 | Koss |
| 4,830,003 A | 5/1989 | Wolff et al. |
| 4,846,836 A | 7/1989 | Reich |
| 4,848,343 A | 7/1989 | Wallsten et al. |
| 4,856,516 A | 8/1989 | Hillstead |
| 4,877,030 A | 10/1989 | Beck et al. |
| 4,878,906 A | 11/1989 | Lindemann et al. |
| 4,886,062 A | 12/1989 | Wiktor |
| 4,907,336 A | 3/1990 | Gianturco |
| 4,913,141 A | 4/1990 | Hillstead |
| 4,921,484 A | 5/1990 | Hillstead |
| 4,922,905 A | 5/1990 | Strecker |
| 4,955,899 A | 9/1990 | Della Corna et al. |
| 4,957,508 A | 9/1990 | Kaneko et al. |
| 4,969,458 A | 11/1990 | Wiktor |
| 4,973,301 A | 11/1990 | Nissenkorn |
| 5,015,253 A | 5/1991 | MacGregor |
| 5,019,090 A | 5/1991 | Pinchuk |
| 5,019,102 A | 5/1991 | Hoene |
| 5,026,377 A | 6/1991 | Burton et al. |
| 5,035,706 A | 7/1991 | Giantureo et al. |
| 5,041,126 A | 8/1991 | Gianturco |
| 5,057,092 A | 10/1991 | Webster, Jr. |
| 5,064,435 A | 11/1991 | Porter |
| 5,067,957 A | 11/1991 | Jervis |
| 5,071,407 A | 12/1991 | Termin et al. |
| 5,078,736 A | 1/1992 | Behl |
| 5,089,006 A | 2/1992 | Stiles |
| 5,108,416 A | 4/1992 | Ryan et al. |
| 5,112,900 A | 5/1992 | Buddenhagen et al. |
| 5,123,917 A | 6/1992 | Lee |
| 5,133,732 A | 7/1992 | Wiktor |
| 5,135,536 A | 8/1992 | Hillstead |
| 5,158,548 A | 10/1992 | Lau et al. |
| 5,176,626 A | 1/1993 | Soehendra |
| 5,221,261 A | 6/1993 | Termin et al. |
| 5,258,000 A | 11/1993 | Gianturco |
| 5,282,823 A | 2/1994 | Schwartz et al. |
| 5,282,824 A | 2/1994 | Gianturco |
| 5,306,300 A | 4/1994 | Berry |
| 5,314,444 A | 5/1994 | Gianturco |
| 5,314,473 A | 5/1994 | Godin |
| 5,316,023 A | 5/1994 | Palmaz et al. |
| 5,316,543 A | 5/1994 | Eberbach |
| 5,330,500 A | 7/1994 | Song |
| 5,334,210 A | 8/1994 | Gianturco |
| 5,360,443 A | 11/1994 | Barone et al. |
| 5,378,239 A | 1/1995 | Termin et al. |
| 5,405,316 A * | 4/1995 | Magram .................. 604/8 |
| 5,405,377 A | 4/1995 | Cragg |
| 5,411,552 A | 5/1995 | Andersen et al. |
| 5,413,601 A | 5/1995 | Keshelava |
| 5,443,499 A | 8/1995 | Schmitt |
| 5,496,277 A | 3/1996 | Termin et al. |
| 5,500,014 A | 3/1996 | Quijano et al. |
| 5,507,771 A | 4/1996 | Gianturco |
| 5,534,287 A | 7/1996 | Lukic |
| 5,545,211 A | 8/1996 | An et al. |
| 5,645,559 A | 7/1997 | Hichtman et al. |
| 5,647,843 A | 7/1997 | Mesrobian et al. |
| 5,653,727 A | 8/1997 | Wiktor |
| 5,662,713 A | 9/1997 | Andersen et al. |
| 5,665,115 A | 9/1997 | Cragg |
| 5,667,523 A | 9/1997 | Bynon et al. |
| 5,674,241 A | 10/1997 | Bley et al. |
| 5,683,448 A | 11/1997 | Cragg |
| 5,716,393 A | 2/1998 | Lindenberg et al. |
| 5,733,325 A | 3/1998 | Robinson et al. |
| 5,733,330 A | 3/1998 | Cox |
| 5,741,333 A | 4/1998 | Frid |
| 5,746,766 A | 5/1998 | Edoga |
| 5,755,769 A | 5/1998 | Richard et al. |
| 5,782,904 A | 7/1998 | White et al. |
| 5,788,626 A | 8/1998 | Thompson |
| 5,817,102 A | 10/1998 | Johnson et al. |
| 5,824,042 A | 10/1998 | Lombardi et al. |
| 5,843,158 A | 12/1998 | Lenker et al. |
| 5,843,170 A | 12/1998 | Ahn |
| 5,861,036 A | 1/1999 | Godin |
| 5,876,445 A | 3/1999 | Andersen et al. |
| 5,876,448 A | 3/1999 | Thompson et al. |
| 5,876,450 A | 3/1999 | Johlin, Jr. |
| 5,879,382 A | 3/1999 | Boneau |
| 5,922,019 A | 7/1999 | Hankh et al. |
| 5,968,070 A | 10/1999 | Bley et al. |
| 5,993,482 A | 11/1999 | Chuter |
| 6,010,529 A | 1/2000 | Herweck et al. |
| 6,027,525 A | 2/2000 | Suh et al. |
| 6,132,471 A | 10/2000 | Johlin, Jr. |
| 6,264,700 B1 | 7/2001 | Kilcoyne et al. |
| 6,302,917 B1 * | 10/2001 | Dua et al. ............ 623/23.68 |

FOREIGN PATENT DOCUMENTS

| | | |
|---|---|---|
| EP | 0857471 | 8/1998 |
| FR | 1576374 | 8/1969 |
| FR | 2513111 | 3/1983 |
| FR | 9101117 | 2/1991 |
| GB | 2069339 | 8/1981 |
| JP | 3-198844 | 8/1991 |
| JP | 7-275369 | 10/1995 |
| JP | 10211287 | 8/1998 |
| RU | 1600785 | 10/1990 |
| WO | 9629954 | 10/1996 |

OTHER PUBLICATIONS

Esophageal Stent with Antireflux Valve for Tumors Involving the Cardia: Work in Progress; M. Köcher, M. Dlouhy, C. Neoral, E. Buriankova, A. Gryga, M. Duda, & R. Aujesky; JVIR; Nov.–Dec., 1998; pp. 1007–1010.

Trial Use of a Gore–Tex Covered Ultraflex Stent with Reflux Preventive Action for Cardioesophageal Cancer; Y. Mizumoto, K. Matsuda, Y. Itoh, M. Kuno, M. Mizumoto, N. Shima, M. Naokl, H. Satake, T. Maekawa, Y. Kajitani & K. Kogawa.

Cook–Z® Stents; Gianturco–Rösch Covered Esophageal Design; Cook Diagnostic and Interventional Products.

* cited by examiner

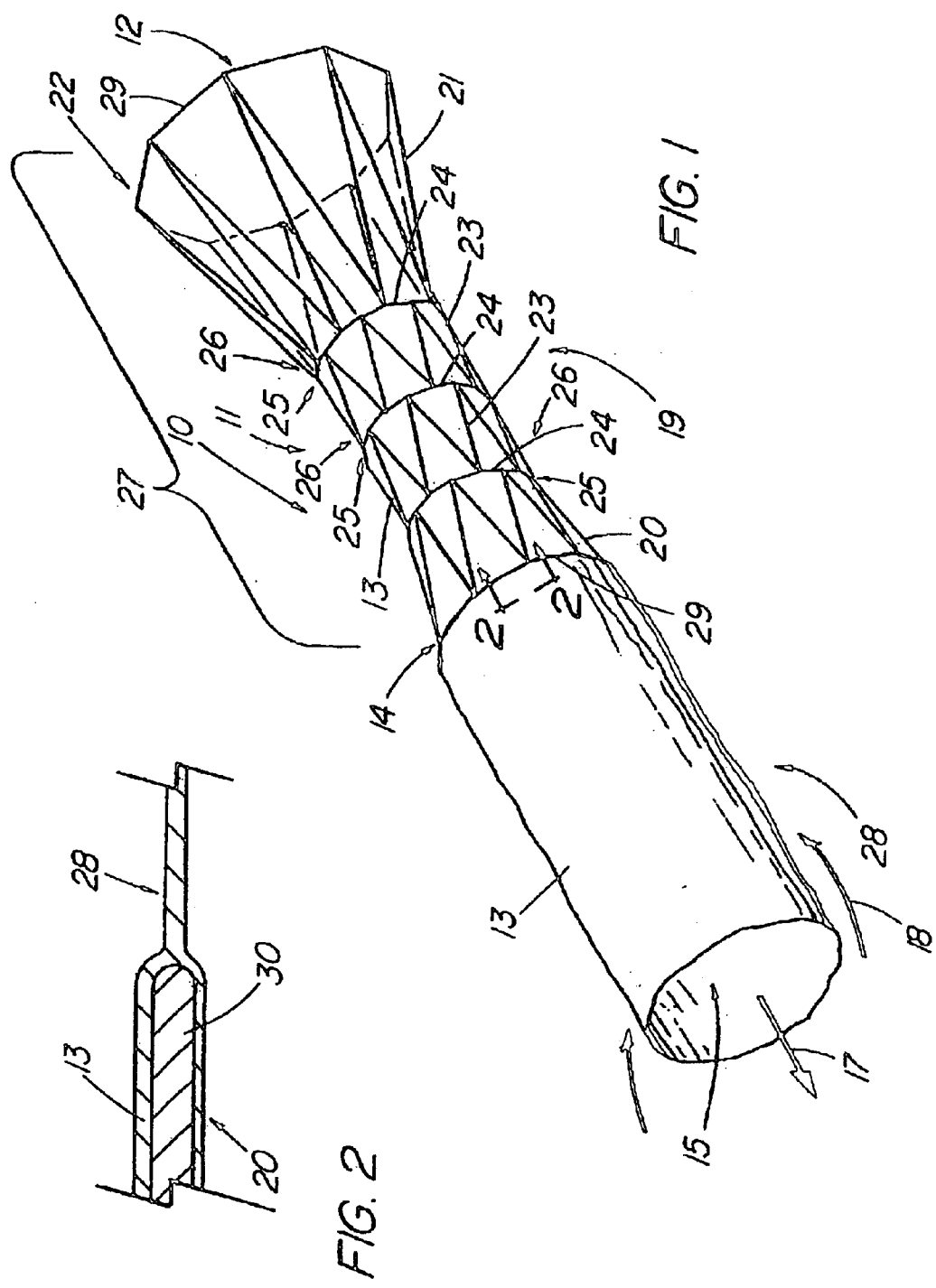

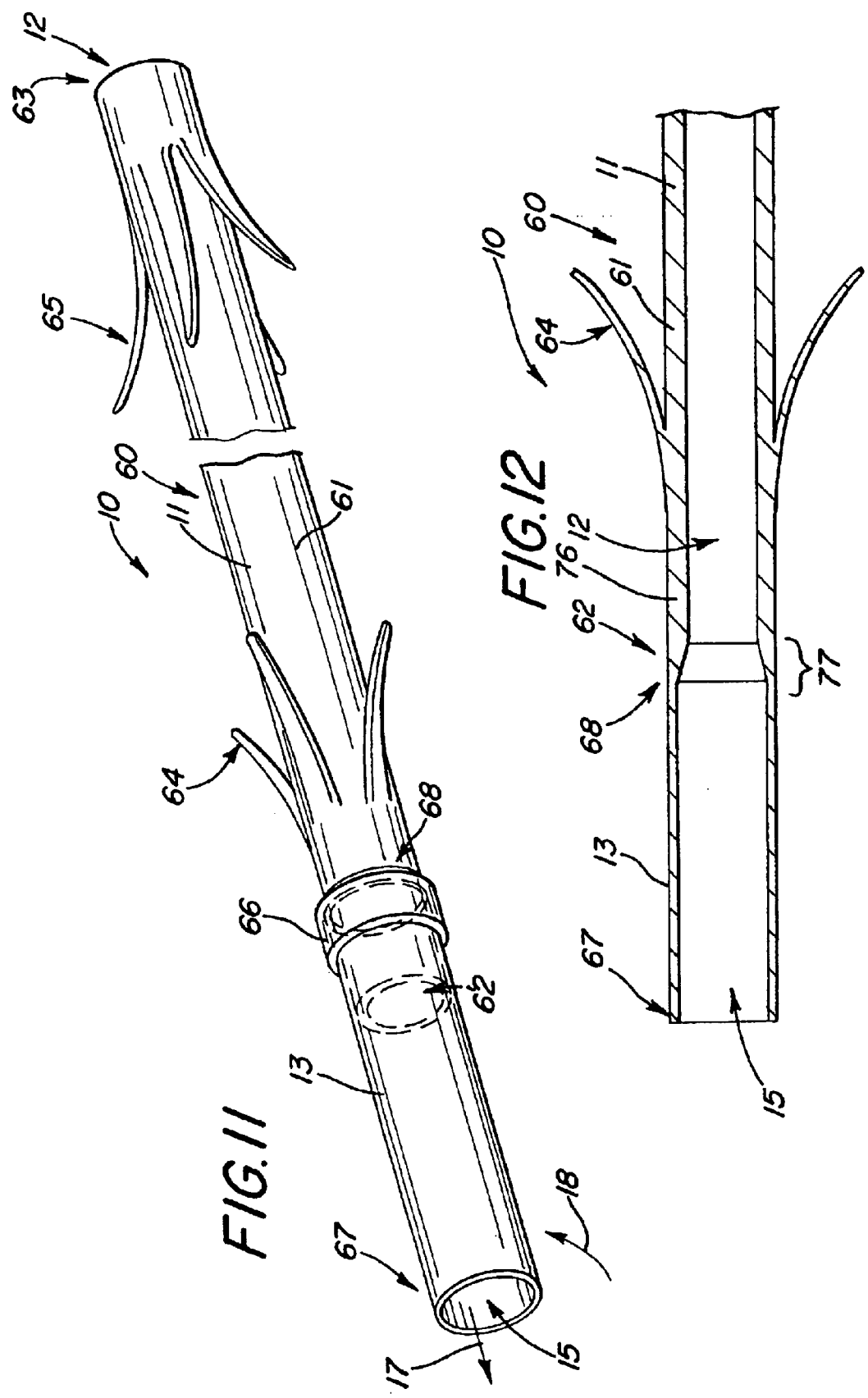

US 6,746,489 B2

PROSTHESIS HAVING A SLEEVE VALVE

CROSS-REFERENCE TO RELATED APPLICATIONS

This application claims priority of provisional application Serial No. 60/211,753, filed Jun. 14, 2000, and is a continuation-in-part of co-pending U.S. patent application Ser. No. 09/386,173, filed Aug. 31, 1999, now U.S. Pat. No. 6,302,917 which claims priority to provisional application Serial No. 60/098,542, filed Aug. 31, 1998.

TECHNICAL FIELD

This invention relates generally to medical devices and, in particular, to an indwelling valved prosthesis.

BACKGROUND OF THE INVENTION

Anti-reflux esophageal prosthesis or stents are typically placed in the lower esophagus and through the lower esophageal sphincter to maintain the patency thereof due to the presence of a cancerous tumor commonly found in the vicinity thereof. The cancerous tumor growth typically impinges the flow of food and fluids through the esophagus. Lower esophageal cancer in the United States presently occurs at the rate of approximately 12,000 patients per year. The incidence in the United States is approximately 5.1 per 100,000 people, which is rising particularly in white male patients. Esophageal prosthesis or stents are typically utilized in these cancerous patients. However, these devices are not FDA approved for benign tumors which also cause blockage or partial stenosis of the esophagus. Esophageal prosthesis or stents are utilized in Europe and other countries for benign tumor conditions, but not in the United States at this time.

A problem with esophageal prosthesis or stents is that fluid from the stomach flows into the mouth of the patient when in a prone position. In an attempt to solve this problem, a number of esophageal prosthesis or stents utilize a one-way valve such as a duck-bill or reed-type valve in which only food or fluid from the esophagus flows into the stomach in only an antegrade or forward direction. However, these one-way anti-reflux prosthesis or stents present another problem. When the patient wants to belch or vomit, he/she is prevented from doing so, because the one-way valve prevents backward flow in the retrograde direction. Such condition is not only painful to the patient, but can also lead to more complicated medical conditions.

There are other anatomical sites, such as the biliary tree or genitourinary system in which a prosthesis may be placed to maintain an open lumen for passage of bodily fluids, thereby creating risk of undesirable retrograde flow and/or migration of pathogenic organisms which could lead to infection or other problems, such as obstruction of the stent. When a drainage stent or catheter is placed across a sphincter or natural stricture at the opening to a bodily passage, the sphincter or stricture cannot fulfill its normal function of restricting retrograde flow or migration. What is needed is a prosthesis and one-way valve that can effectively regulate antegrade and retrograde flow in response to the normal flow rates and pressures that exist across the site in which the prosthesis is placed.

SUMMARY OF THE INVENTION

The foregoing problems are solved and a technical advance is achieved in an illustrative prosthesis having a sleeve which permits antegrade flow under a first pressure through the sleeve, and collapses in response to a second flow or pressure that is greater than the first flow or pressure.

In one aspect of the invention, the prosthesis comprises an anti-reflux esophageal prosthesis in which a sleeve extending from a tubular frame thereof inverts through the passage of the tubular frame and allows stomach gas or vomit to flow in a retrograde direction when the pressure in the stomach exceeds a given level. In the antegrade or downward position, the sleeve collapses and prevents the reflux of stomach gas and fluid from flowing through the esophagus and into the mouth of the patient. The collapsible sleeve functions as a one-way valve and allows the patient to ingest or pass liquid and food therethrough and into the stomach. In addition, the tubular frame of this advantageous anti-reflux esophageal prosthesis maintains the patency of the lower esophagus and sphincter particularly when a cancerous tumor impedes fluid flow through the esophagus.

In another advantageous aspect of the present invention, the tubular frame of the anti-reflux esophageal prosthesis includes a plurality of self-expanding zig-zag stents. The compressed stents along with the sleeve are positioned in an delivery catheter which is orally passed through the esophagus and lower sphincter. The prosthesis is then deployed from the delivery catheter with, for example, a dilator or pusher catheter that is inserted in the lumen of the delivery catheter. The deployed, self-expanding stents readily expand to engage the esophagus and lower sphincter and maintain them in a patent condition.

The self-expanding stents of the tubular frame are also advantageously flared at each end of the tubular frame to prevent antegrade and retrograde migration of the expanded prosthesis. To further prevent migration of the zig-zag stents with respect to each other, a filament is circumferentially positioned through closed eyelets at the bends of adjacent zig-zag stents. The filaments are also utilized advantageously to control the radial expansion and the flared configuration of the stents positioned at the ends of the tubular frame.

The pressure needed to collapse or invert the one-way valvular sleeve is a function of the sleeve material, its wall thickness and length extending from the distal end of the tubular frame. Depending on the anatomical size of the human or veterinary patient, the sleeve can extend from the end of the frame for a length in a range of from 0.0 to 20 cm, preferably in a range of 5 to 15 cm; and more preferably in length of approximately 10 cm in a human patient or 8 cm in a veterinary patient as experimentally derived therefor. The sleeve material also advantageously includes a material of polyurethane, silicone, polyamides, other urethanes or any biocompatible material that is flexible and acid resistant. The sleeve material can have an advantageous thickness of 0.005" through 0.008". This thickness is at the portion covering the frame itself. The sleeve extending from an end of the frame comprises a material having a thickness in a range of 0.0015" to and including 0.004" and preferably approximately 0.002". Advantageously, the length of the sleeve is made long enough so that it can be readily shortened to accommodate individual anatomical situations.

In another aspect of the invention the collapsible sleeve is attached to a tubular drainage stent, such as a biliary stent, to advantageously prevent reflux of intestinal contents and the associated bacteria into the passage of the stent. These bacteria are known to promote the formation of biofilm which can lead to occlusion of the stent. With the stent placed in the biliary tree for maintaining patency of the bile or pancreatic duct and the Papilla of Vater, the sleeve extends down into the duodenum to provide a one-way valve for the flow of bile. When bile is not being secreted, the sleeve advantageously collapses to prevent backflow of material from the duodenum, a situation which might otherwise occur in a biliary stent without a closure means. Tubular drainage stents for placement in the ureters or urethra can include either a sleeve extending from one end to permit urine flow and prevent retrograde flow or pathogen migration toward the kidneys or bladder, or the sleeve may be located completely within the lumen of the drainage stent with one end of the sleeve being bonded or otherwise attached to the inner walls of the lumen.

BRIEF DESCRIPTION OF THE DRAWINGS

FIG. 1 depicts a pictorial view of an illustrative embodiment of a pressure sensitive anti-reflux esophageal prosthesis of the present invention;

FIG. 2 depicts an enlarged cross-sectional view of a sleeve about a cylindrical wire of a flared stent of the esophageal prosthesis taken along line 2—2 of FIG. 1;

FIG. 11 depicts a pictorial view of an embodiment of a tubular drainage prosthesis of the present invention;

FIG. 12 depicts a cross-sectional view of a second embodiment of a tubular drainage prosthesis;

DETAILED DESCRIPTION

Figure 3:
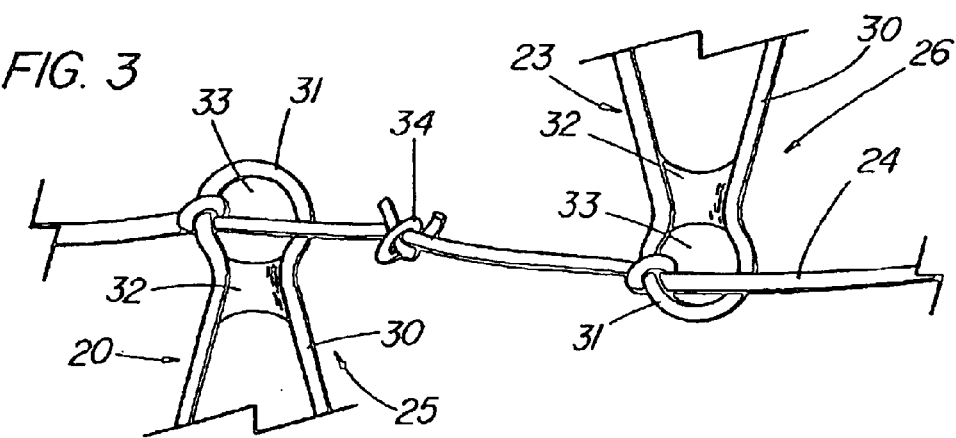
FIG. 3 depicts an enlarged partially sectioned view of the adjacent ends of interconnected stents of the prosthesis of FIG. 1.

FIGS. 1–14 depict exemplary prostheses of the present invention comprising a tubular member 11 with a passage 12 therethrough, and a thin, flexible sleeve 13 extending from the tubular member 11. The sleeve 13, which also has a passage 15 therethrough, is configured to allow the flow of liquid or other materials moving under a first pressure until the flow and pressure are lessened where they are exceeded by the second, back pressure of the drainage environment, at which time the sleeve 13 collapses to prevent the ingress of fluids of materials into the tubular member.

FIG. 1 depicts a pictorial view of an illustrative, preferred embodiment of pressure sensitive anti-reflux esophageal prosthesis 10 of the present invention. The prosthesis includes a tubular frame 11 of a plurality 19 of self-expanding, zig-zag wire stents 20, 21, and 23 covered by a polyurethane sleeve 13 that is disposed around and extends along entire length 27 of the tubular frame. The sleeve also extends from distal end 14 of the self-expanding tubular frame and has a lumen 15 extending longitudinally therethrough. Lumen 15 of the sleeve also communicates with passage 12 of the tubular frame. When the prosthesis is positioned in the lower esophagus and through the lower sphincter of a patient, lumen 15 in lower portion 28 of the sleeve collapses upon itself due to wetting by gastric juices, fluid or saliva flowing therethrough from the esophagus in a first direction 17. As a result, sleeve 13 is in a collapsed position and acts as a one-way valve into the stomach, thereby preventing the reflux of gastric fluid from flowing in a retrograde manner through the prosthesis and esophagus and into the mouth of the patient, referred to herein as the second direction 18. However, fluid readily flows in the opposite (first) direction 17 from the esophagus and through the one-way valve sleeve into the patient's stomach.

Tubular frame 11 includes plurality 19 of self-expanding stents 20, 21, and 23 that are interconnected circumferentially by filament 24 about adjacent ends 25 and 26 of the stents. In this illustrative embodiment, the tubular frame includes four self-expanding, zig-zag wire metal stents of the Gianturco type as described in U.S. Pat. No. 4,580,568, which is incorporated by reference herein. Tubular frame includes first and second flared stents 20 and 21 positioned at distal and proximal ends 14 and 22 with first and second cylindrical stents 23 positioned therebetween. By way of example, first and second flared stents 20 and 21 have a minimum diameter of 18 mm and a flared diameter of approximately 25 mm. These diameters are nominal diameters for the stents and can be customized to meet the particular demands of any human or veterinary patient. The diameter of the flared end is maintained by end filament 29. The minimum diameter of the flared stents along with the nominal diameter of the cylindrical stents is maintained by interconnecting filaments 24. The interconnecting and end filaments 24 and 29 are, for example, 3/0 diameter mononylon suture material. The first and second flared stents 20 and 21 are positioned below and above the lower esophageal sphincter and prevent the migration of the prosthesis in either the antegrade or retrograde direction with respect to the esophagus. The flared proximal stent along with the cylindrical stents 23 also expand against any tumor that is in the region of the lower esophagus and maintains the patency of the lower esophageal lumen.

Flared stents 20 and 21 are, for example, formed from commercially available Series 304 stainless steel cylindrical wire having a diameter of approximately 0.015". The wire is formed into a zig-zag pattern of which the ends are joined together using, for example, a metal sleeve and soldered together using silver/tin solder. However, other ways of forming a closed zig-zag configuration that resembles at least a partially tubular shape is contemplated. The flared or maximum diameter of the flared stents is approximately 25 mm with the minimum diameter at approximately 18 mm. Interconnecting cylindrical stents 23 are also formed from the same cylindrical wire and have a nominal diameter of approximately 18 mm matching that of the minimum diameter of the flared stents. The length of the individual stents is approximately 2 cm. The overall length of the tubular frame can range from 8 to 14 cm in 2 cm increments. These 2 cm increments are typically provided by increasing the number of interconnecting cylindrical stents 23.

Sleeve 13 preferably comprises a polyurethane material or other liquid impermeable material that does not degrade in the presence of fluids or gastric material that comes in contact therewith. The sleeve is disposed around and extends at least partially around tubular frame 11. Preferably, the sleeve extends the entire length of the frame and extends longitudinally from distal end 14 of the tubular frame. The length of the sleeve material extending from the distal end of the tubular frame can range from 0 through 20 cm, preferably 5 to 15 cm, and more preferably 10 cm. The length of the sleeve material can be individually customized by the physician depending on the anatomy of the patient. Experimental data has indicated that dogs typically utilize a 7 cm length of sleeve material. Human patients are expected to utilize a sleeve length of 8 or 9 cm. However, the length can again be modified by the physician to meet the particular anatomy of the patient. The wall thickness of the sleeve material disposed around the tubular frame is approximately 0.006" thick. The thickness of the sleeve material along lower portion 28 of the sleeve is approximately 0.002" thick. The sleeve material preferably includes a medical grade polyurethane material; although silicone, nylon, polyamides such as other urethanes, or other biocompatible material that is flexible and acid resistant are also suitable materials. In particular, the polyurethane of the present invention is a medical grade polyurethane material grade EG-80A material commercially known as TECOFLEX® polyurethane material from Thermedics, Incorporated, Woburn, Mass.

FIG. 2 depicts an enlarged sectioned end view of sleeve 13 about cylindrical wire 30 of flared stent 20 of FIG. 1 along the line 2—2. As shown, the thickness of the sleeve material is approximately 0.006", whereas the thickness of the sleeve material along lower or distal portion 28 thereof is preferably and approximately 0.002". The thickness of sleeve material above distal portion 28 ranges from 0.005" through 0.008". Experimental data has indicated that the sleeve material along distal portion 28 still collapses at 0.004" wall thickness so as to effectively form a one-way valve. Closure of the one-way valve sleeve material occurs at thicknesses above 0.004"; however, closure does not occur on a guaranteed basis each time. The thickness of the sleeve wall material below 0.0015" presents a problem of tearing particularly when inserting the prosthesis into a delivery catheter.

FIG. 3 depicts an enlarged partially sectioned view of adjacent ends 25 and 26 of interconnected stents 20 and 23 of FIG. 1. Bends 31 of cylindrical wire 30 are formed into a keyhole configuration with silver solder 32 interconnecting the wire arms, thereby forming an aperture or eyelet 33. Interconnecting filament 24 is positioned through each eyelet and wound around at least once to aid in fixing the diameter of the expandable stents. One interconnecting or end filament is used at the end of each stent and tied at the loose ends with suture knot 34.

Figure 4:
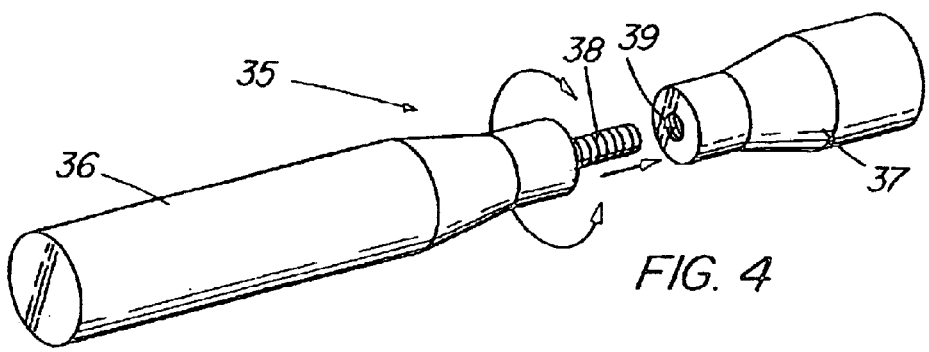
FIG. 4 depicts a two piece mandril that is used to apply the sleeve material to the prosthesis of FIG. 1.

FIG. 4 depicts two piece mandril 35 that is used to apply sleeve material 13 to the prosthesis of FIG. 1. The mandril includes sleeve portion 36 and upper frame portion 37 that are interconnectable with, for example, threaded rod 38 and internally threaded channel 39. In use, the tubular frame including the plurality of self-expanding wire stents are positioned end-to-end and interconnected using interconnecting filament 24. The end filament is also positioned through the eyelets of the flared stents to control the maximum diameter thereof. The mandril has a minimum inner diameter matching that of the inside diameter of the inner stents and a flared diameter matching that of the flared stents. Extending from the ends of the flared portions, the mandril assumes the inner diameter of the one-way valve sleeve material. The assembled tubular frame is positioned between the upper frame portion of the sleeve portion of the mandril. The two portions of the mandril are then interconnected, thereby filling up the passage of the tubular frame. The tubular frame is then dipped into a slurry material of polyurethane to form an initial 0.004" thickness over the entire length of the tubular frame. The mandril and covered tubular frame are then dipped in the slurry material at least one additional time to form the desired thickness of the sleeve material over mandril sleeve portion 36. After the slurry material cures, the two portions of the mandril are disconnected to form the anti-reflux esophageal prosthesis.

Figure 5:
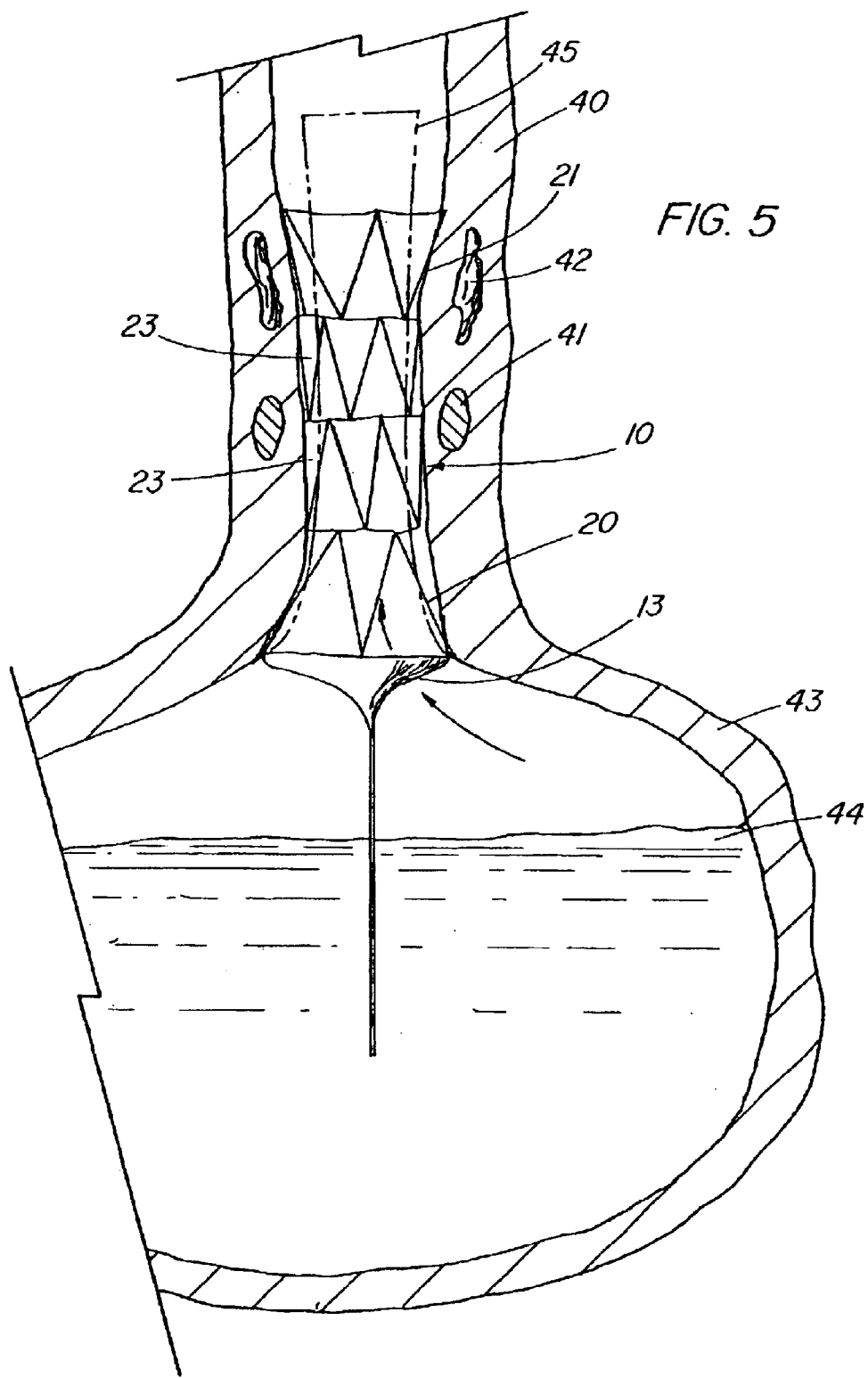
FIG. 5 depicts the esophageal prosthesis of FIG. 1 deployed in the lower esophagus of a patient, and, in particular, through the lower esophageal sphincter and a cancerous tumor.

FIG. 5 depicts esophageal prosthesis 10 deployed in lower esophagus 40, and, in particular, through lower esophageal sphincter 41 and cancerous tumor 42. Distal flared stent 20 typically extends into the stomach along with sleeve 13. Flared stent 21 is positioned proximal to the sphincter and tumor, whereas the interconnected cylindrical stents are typically positioned through the sphincter and tumor. The flared stents 20 and 21, again, prevent a migration of the prosthesis in the esophagus. The lower or distal portion 28 of sleeve 13 extends into stomach 43. The lumen of the lower sleeve portion readily collapses when in contact with any external fluid applied thereto. However, any liquid or food is readily passed in an antegrade direction through the esophageal stent and into the stomach. As a result, one-way valve sleeve 13 opens to provide flow in the antegrade direction. Conversely, any fluids or food material 44 are prevented from flowing into the retrograde direction due to the collapsed lumen of sleeve 13. However, when the pressure of the gas or fluid in the stomach builds so as to cause the patient to belch or vomit, sleeve 13 will invert and extend in an antegrade direction through the lumen of the tubular frame as shown by phantom lines 45. In this position, gastric fluid and matter flows in the retrograde direction to relieve the patient. The length of distal portion 28 of the sleeve and the thickness thereof control the pressure at which the distal portion of the sleeve inverts through the tubular frame.

Self-expanding esophageal prosthesis are increasingly being used for palliation of malignant dysphagia. They can predispose to significant gastroesophageal reflux, including risk of aspiration, when deployed across the gastroesophageal junction. A study was performed to evaluate the anti-reflux efficacy of a esophageal prosthesis of the present invention to prevent reflux. A model EZS 21-8 from Wilson-Cook Inc., Salem, N.C. (16 mm diameter) was modified by extending its polyurethane covering 7 cm beyond its distal metal cage so as to form a "windsock" or collapsible sleeve. The pressure required to invert the windsock or collapsible sleeve into the tubular frame (reflux barrier) was determined by attaching the proximal end of the prosthesis to a hollow graduated tube and vertically inserting the stent under water until the windsock inverted. The pressure required to revert the windsock or collapsible lumen to its original one-way position was determined by pouring water into the lumen of the prosthesis. In-vivo evaluation was done in two esophagostomized dogs (male—18 kg, female—16 kg) and prosthesis insertion, positioning, and removal done by standard endoscopic and fluoroscopic techniques. Two site ambulatory esophageal pH monitoring (Synectics Medical) was performed at 5 cm and 10 cm above the gastroesophageal function. Each dog was studied twice using the standard model EZS 201-8 prosthesis and twice using the modified prosthesis (mean recording time per session 18.7+/−1 SE and 17+/−3 hours respectively). The results indicated that the windsock modification posed no difficulty in mounting or deploying the prosthesis using a currently available delivery system. Resistance to antegrade flow was minimal as even a drop of water put into the prosthesis easily passed through the windsock and both the dogs drank all the Ensure (4 cans per session) given to them irrespective of the type of prosthesis used. The pressure (cm of water) to overcome the reflux barrier was 15.7+/−0.3 SE and that to revert an inverted windsock or collapsible lumen was 0.4+/−0.03 SE. Results of the pH monitoring (mean+/−SE) is depicted in Table 1.

TABLE 1

|  | Standard Stent | | Anti-reflux Stent | |
| --- | --- | --- | --- | --- |
| Recording site (cm) above GEJ | 5 | 10 | 5 | 10 |
| Number of reflux episodes | 229 ± 25" | 56 ± 9 @ | 9.7 ± 7* | 8 ± 5 @ |
| Fraction time pH < 4 (%) | 60 ± 5* | 7.6 ± 2 @ | 0.7 ± 0.3* | 0.2 ± 0.1 @ |

Figure 8:
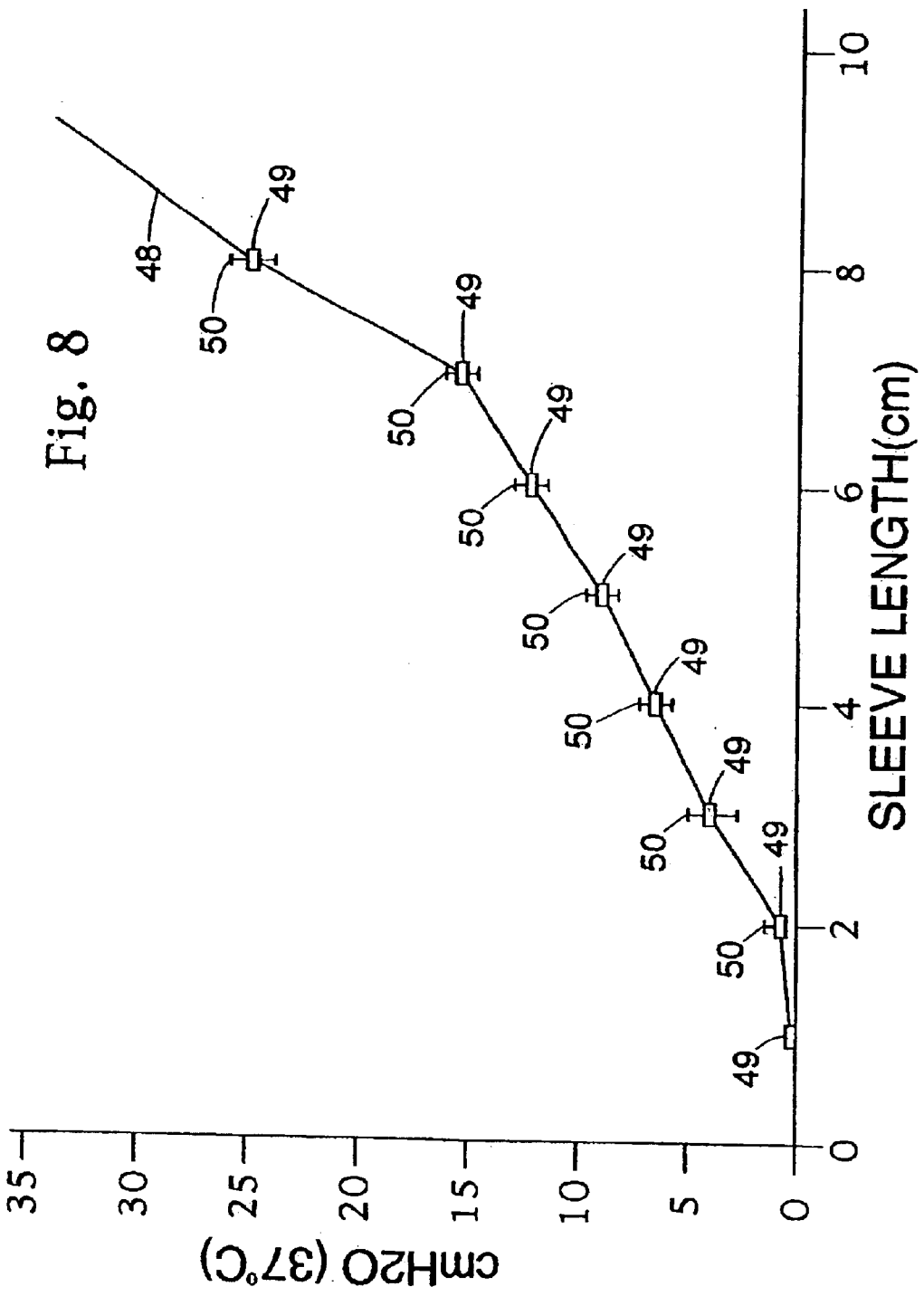
FIG. 8 depicts an in-vitro barrier reflux curve for an anti-reflux esophageal prosthesis of the present invention.
Figure 10:
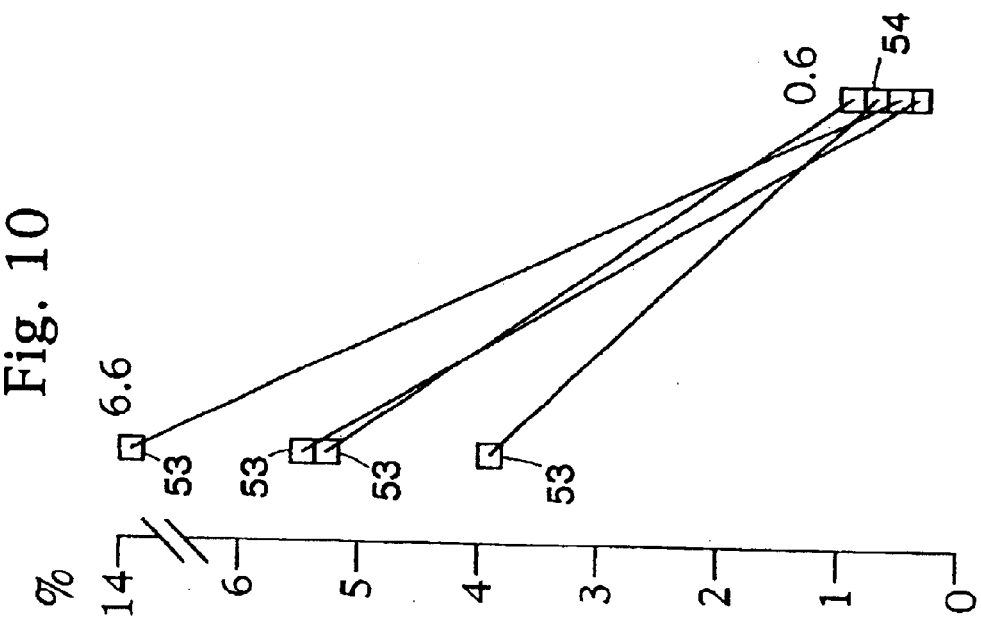
FIGS. 9 and 10 depict the percent of fraction time of standard and anti-reflux esophageal prosthesis utilized in an evaluation of the present invention.
Figure 9:
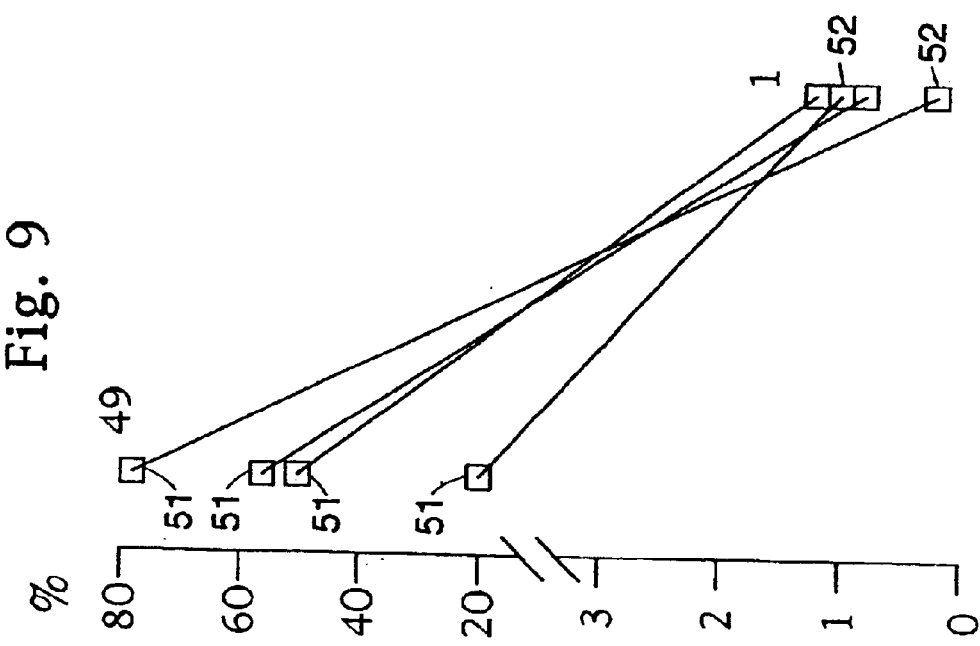

The conclusions reached in the experiment were that a modified self-expanding metal esophageal prosthesis is highly effective in preventing reflux. The ability of the windsock or collapsible lumen sleeve 13 to invert at higher pressure gradients can allow patients to belch or vomit. Reversion to anti-reflux position requires minimal pressure and can be achieved by a water swallow. Further studies are indicated in FIGS. 8–10.

Figure 6:
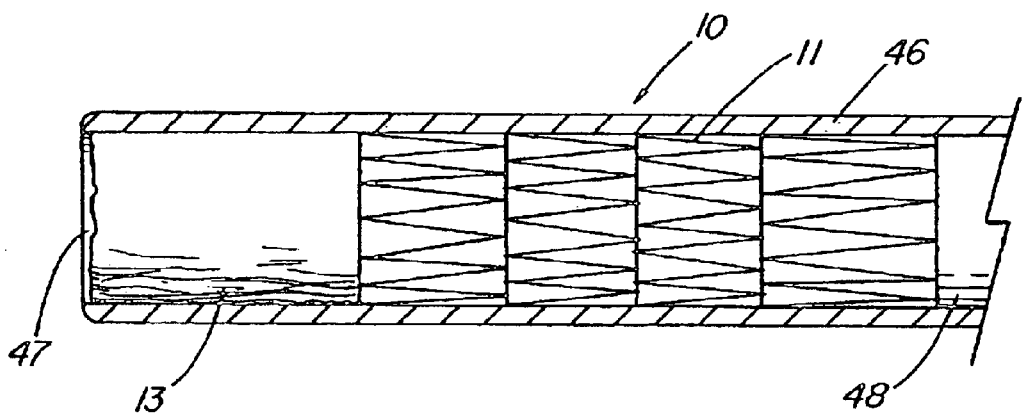
FIG. 6 depicts the anti-reflux esophageal prosthesis of FIG. 1 in a collapsed state in a delivery catheter.

FIG. 6 depicts anti-reflux esophageal prosthesis 10 of FIG. 1 in a collapsed state in delivery catheter 46. Sleeve material 13 is positioned at the distal end of the delivery catheter. The prosthesis is drawn into the delivery catheter with a drawstring attached at the proximal end of the prosthesis. The drawstring and prosthesis are inserted through lumen 47 of the catheter by collapsing the tubular frame and then pulling the prosthesis into the distal end of the delivery catheter with the drawstring. To deploy the collapsed prosthesis from the delivery catheter, a pusher catheter 48 is positioned proximally in lumen 47 to engage the proximal end of the wire tubular frame 11.

Figure 7:
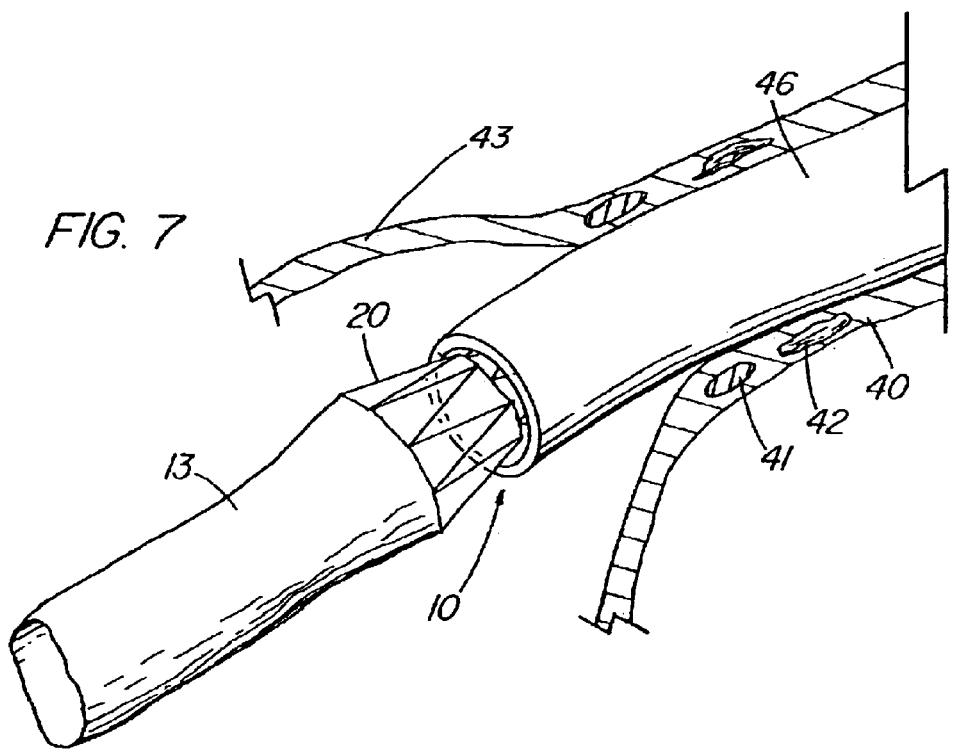
FIG. 7 depicts the delivery catheter of FIG. 6 positioned in the lower esophagus, sphincter, and tumor of a patient.

FIG. 7 depicts delivery catheter 46 of FIG. 6 positioned in lower esophagus 40, sphincter 41, and tumor 42 of a patient. The distal end of the delivery catheter extends into stomach 43. As shown, the pusher has been placed in the lumen of the delivery catheter and engages the proximal end of prosthesis 10. As shown, sleeve 13 and flared distal stent 20 have been deployed from the distal end of the catheter. After the sleeve and distal flared stent 20 of the prosthesis have been deployed, the delivery catheter is partially withdrawn so as to engage the flared stent with the neck of the stomach about sphincter 41. Once positioned, the delivery catheter is pulled back while maintaining the position of the pusher catheter therein so as to release the central cylindrical stents and proximal flared stent against the sphincter, tumor, and lower esophagus.

An in-vitro and in-vivo evaluation of a modified self-expandable metal esophageal stent with an anti-reflux mechanism of the present invention was performed on a number of dogs. The evaluation included four dogs, two of which were males at 14 and 18 kg and two females at 14 and 16 kg. An esophagostomy was utilized with the use of upper gastro-intestinal endoscopy. The evaluation included the methods of ambulatory pH monitoring with the use of Synectics medical equipment at 5 and 10 cm with Gastrograph Inc. software. A liquid diet of Ensure at a pH of 6.5 was administered. The results of the employed methods are included in Table 2.

TABLE 2

|  | Standard Stent | Anti-Reflux Stent | P |
| --- | --- | --- | --- |
| Duration of pH Monitoring (hrs. mins) | 20.30 ± 1.6 | 21.38 ± 0.9 | ns |
| Oral Intake Ensure (ml) | 1007 ± 0.5 | 978 ± 0.4 | ns |

FIG. 8 depicts in-vitro reflux barrier curve 48 which illustrates the water column height in centimeters necessary to invert a given sleeve length extending from the distal end of the prosthesis. Rectangular median value boxes 49 indicate the median value of the water column height at the indicated sleeve lengths. The vertical bar 50 positioned on curve 48 with rectangular median value boxes 49 represent a standard deviation above and below the indicated median value. In addition, the number of reflux episodes was monitored at the distal and proximal ends of the prosthesis. With a standard prosthesis without a one way valve, 197 episodes of reflux were encountered in 250 attempts. At the proximal end of the standard tubular esphageal prosthesis, a total of 33 reflux episodes were noted with 50 attempts. Correspondently, only 16 reflux episodes were noted out of 250 attempts at the distal end of an anti-reflux esophageal prosthesis of the present invention. At the proximal end of the anti-reflux esophageal stent only 8 episodes out of 50 attempts were noted. The number of reflux episodes longer than five minutes was also noted. In the standard prosthesis, 19.8 episodes were recorded for 25 attempts. This is in contrast to 0.3 episodes for an anti-reflux esophageal stent of the present invention. At the proximal end of the prosthesis, 2.3 episodes lasting longer than five minutes were noted with three attempts; whereas none were noted with the anti-reflux prosthesis. The longest reflux episodes were also noted at the distal and proximal ends of the standard and anti-reflux prosthesis. For the standard prosthesis, 107 episodes were noted out of approximately 130 attempts; whereas only 3.8 were noted for the anti-reflux prosthesis at the distal end thereof. At the proximal end of the prosthesis, 39 episodes were noted out of 45 for the standard prosthesis; whereas only 1.8 for the anti-reflux prosthesis were noted.

FIG. 9 depicts the fraction time percentages of which the esophagus was exposed to gastric juice with a pH less than 4. At the distal end of the prosthesis, the percentage of fraction time is indicated by boxes 51 for the four dogs at the distal end of the standard prosthesis. These percentage fraction times range from 20–80% with a median value of 49%. For the anti-reflux prosthesis, the percentage of fraction time ranges from 0.0 to approximately 1.5% with a median value of 1% as indicated by boxes 52. The p-values for these fractions times is 0.026.

FIG. 10 depicts the fraction time percentages at the proximal ends of the standard and anti-reflux prosthesis. Boxes 53 represent the percent fraction time for the standard prosthesis which ranges from approximately 4–14% with a median of 6.6%. Rectangular boxes 54 represent the percent fraction time for the anti-reflux prosthesis which range from approximately 0.0 to 1.0%. These have a p-value of approximately 0.055.

The conclusions resulting from this in-vitro and in-vivo evaluation are as follows. The modified self-expanding metal esophageal stent of the present invention is highly effective in preventing gastro-esophageal reflux. The ability of the modification to invert at higher pressure gradients allows for belching and vomiting. Once inverted, reversion to the anti-reflux position of the prosthesis requires minimal pressure that can be achieved by a water swallow.

In a second embodiment of the present invention depicted in FIGS. 11–14, the prosthesis 10 and tubular member 11 comprise a tubular drainage stent 60 having a first end 62 for drainage into a duct, vessel, organ, etc., and a second end 63 that receives the fluid or other material that is moving under a first, antegrade pressure and direction 17. As defined, a tubular drainage stent (or tubular drainage catheter) is typically an elongate, closed tubular conduit (typically plastic or metal) that is placed within a bodily passage, such as the bile duct, pancreatic duct, urethra, etc. to facilitate the flow of fluids therethrough. It is typically non-expanding, unlike a the wire or open-frame stents of FIGS. 1–10. It is commonly placed either to establish or maintain patency of the bodily passage or to drain an organ or fluid source, such as the gall bladder or urinary bladder. The tubular drainage stent may also include a retention means 64,65 at one or more ends 62,63, such as flaps, barbs, pigtail loops, etc. The tubular drainage stent 60 is attached to the collapsible sleeve 13, which acts as a one-way valve to prevent retrograde flow 18 therethrough. The first end 67 of the sleeve is maintained open when the fluid or material passing through the sleeve is exhibiting a pressure associated with normal antegrade flow 17. The first end 67 collapses shut when the antegrade flow 17 has ceased or lessened such that the second fluid pressure 18 occurring in the environment into which the fluid is drained becomes higher than the first pressure of the antegrade flow 17. In the illustrative biliary stent embodiment, bile is able to flow into the duodenum 71, but the sleeve 13 closes in the absence of measurable flow 17, thus preventing the contents of the intestinal tract, which now have a second, higher pressure 18, from entering the passageway of the stent. The sleeve 13 is made of a biocompatible material that will not degrade when placed in the particular environment of the human body into which it is to be placed. Possible materials include expanded polytetrafluoroethylene (ePTFE), polyurethane, silicone, nylon, polyamides such as other urethanes, or other biocompatible materials. It is important that the sleeve material be selected appropriately. For example, in the illustrative embodiment, the sleeve is typically made of a 2–3 cm section of ePTFE which is much more resistant to the caustic bile than would a sleeve of polyurethane. The ePTFE tube is extruded into a thin wall tube having sufficient flexibility to collapse and seal against the ingress of fluid, while having sufficient integrity to resist tearing. The normal range of sleeve thickness for the illustrative embodiment is 0.001 to 0.01 in., with a more preferred thickness of 0.002 to 0.005 in (e.g., 0.0025). The second end 68 of the sleeve is attached about the first end 62 of a biliary stent 60, such as a ST-2 SOEHENDRA TANNENBAUM® stent, a COTTON-LEUNG® stent or a COTTON-HUIBREGTSE® stent (Wilson-Cook Medical Inc., Winston-Salem, N.C.), by an attachment means 66, such as an illustrative crimped metal band. This band 66 can be made radiopaque to also serve as a fluoroscopic marker. Other methods of attachment could include, suture binding, selected medical grade adhesives, or thermal bonding, if appropriate for both the sleeve and stent polymers.

An alternative method of forming the sleeve for a tubular drainage stent 60 is depicted in FIG. 12. Rather than attaching a separately extruded or preformed sleeve 13 to the tubular member 11, the wall of the tubular member, which is made of polyethylene in this embodiment, is thinned out distally from the first end 62 of the tubular drainage stent 60, such that the sleeve 13 is integral with the tubular member 11. A transition zone 77 exists between the first end tubular drainage stent 60 and the second end 68 of the sleeve 13, beyond which the sleeve 13 becomes sufficiently thin to collapse into a closed position in the absence of antegrade flow 17, such as bile.

Figure 13:
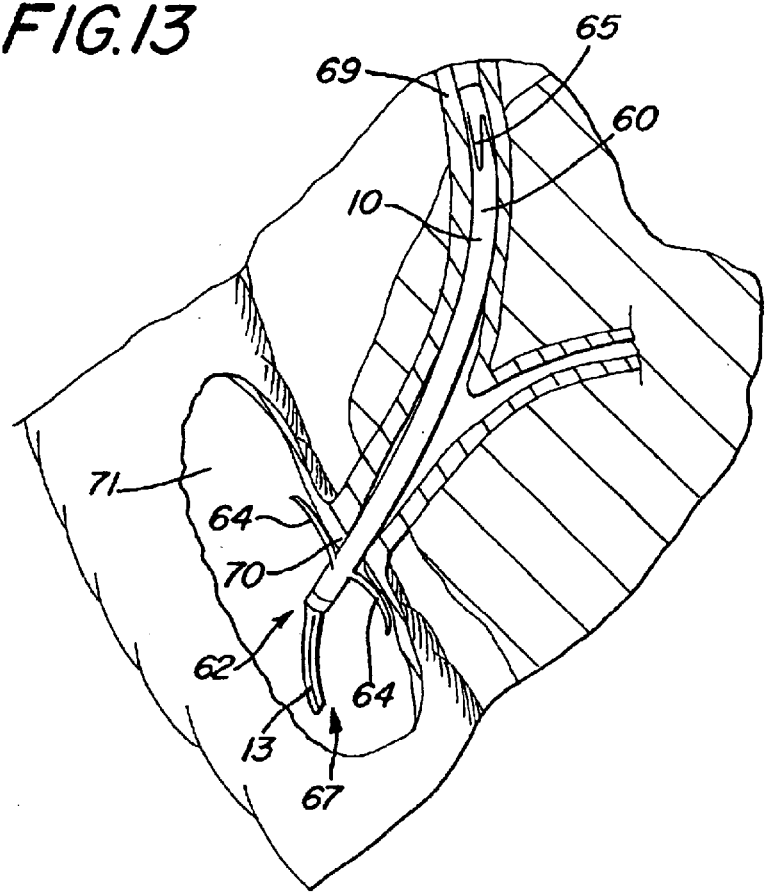
FIG. 13 depicts the prosthesis of FIG. 11 positioned in the common bile duct of a patient.
Figure 14:
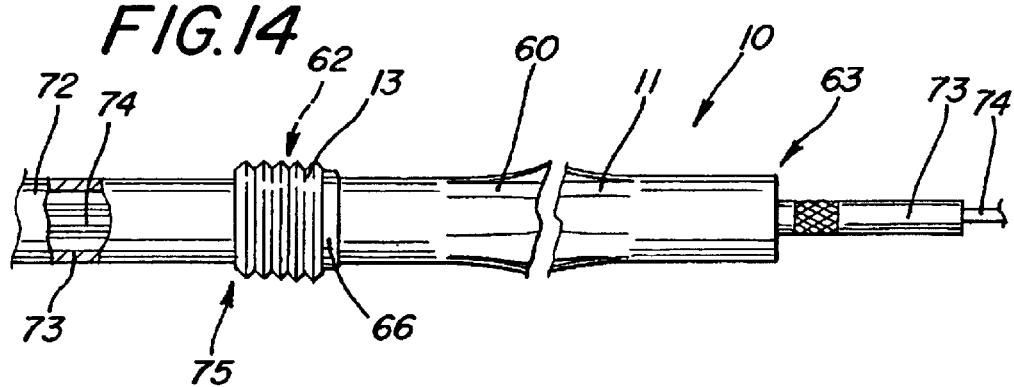
FIG. 14 depicts a side view of the prosthesis of FIG. 11 mounted on a delivery system.

FIG. 13 depicts how the illustrative embodiment is used within the common bile duct 69 to permit the drainage of bile across the Papilla of Vater 70 and into the duodenum 71. The biliary stent 60 is positioned in the normal manner inside the common bile duct 69 with the first end 62 of the stent extending outside of the duct and Papilla of Vater 70. The first retention means 64 abuts the opening of the sphincter to prevent ingress of the stent 60 into the duct while the second retention means 65, located about the second end 63, is positioned well inside the duct to prevent the stent 60 from migrating outward. The sleeve 13 lies completely within the duodenum where it acts as a one-way valve to prevent intestinal contents from entering the biliary stent 60. Unlike the embodiment of FIG. 1, the sleeve 13 is not designed to invert back through the tubular member 13 in the presence of a third, significantly higher pressure, a situation which is normally not found inside the duodenum, or even clinically necessary as with the esophageal embodiment where belching or vomiting make such a capability desirous. Placement of the embodiments of FIGS. 11–12 can be accomplished by a system such as that depicted in FIG. 14. The biliary stent 60 is mounted on a guiding catheter 73 which is fed over an standard biliary exchange wire guide 74 into the bile duct. To deploy the stent from over the guiding catheter 73, a pusher element 72 is used with the distal end 75 of the pusher contacting the first end 62 of stent 60 and urging it forward until deployment occurs. The sleeve 13 is normally folded in accordion fashion prior to deployment, whereby it resumes its elongate configuration once the prosthesis 10 has been properly positioned.

Figure 15:
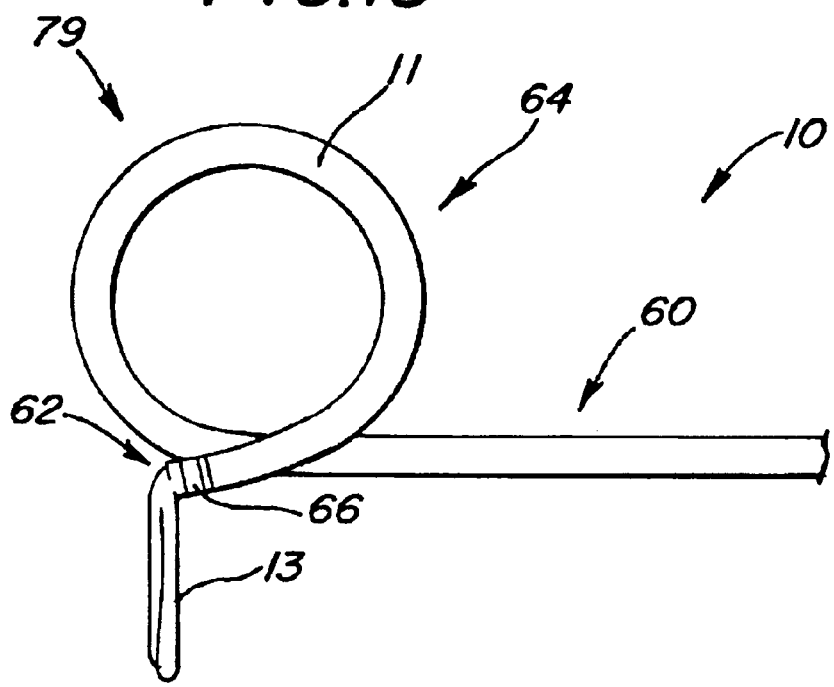
FIG. 15 depicts a side view of one end of a valved prosthesis that includes a pigtail configuration.

FIG. 15 depicts a prosthesis 10 comprising a tubular drainage stent 60 that is configured for placement in the urinary system, such as within the ureter between the kidney and the bladder. The sleeve 13 is attached to the first end 62 of the tubular drainage stent 60, which includes a first retention means 64 that comprises a pigtail configuration 79. In a ureteral stent, the pigtail 79 would be placed within the bladder to prevent migration of the stent. Optionally, a pigtail configuration 79 can be used to anchor the second end of the stent (not shown), typically within the ureteropelvic junction. The pigtail configuration is exemplary of a large variety of well know pigtail ureteral and urethral stents.

Figure 16:
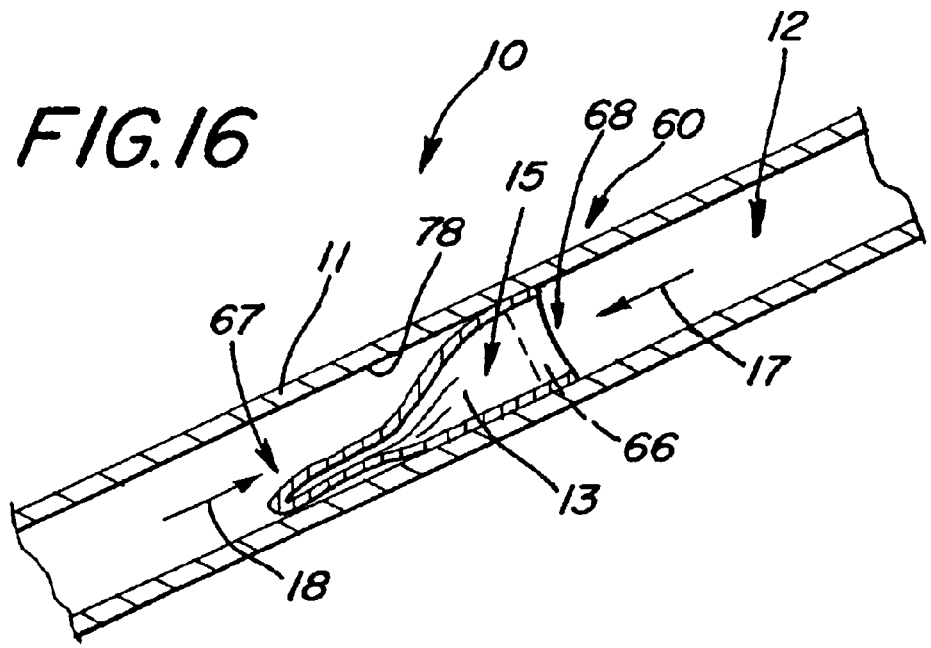
FIG. 16 depicts a laterally sectioned view of a valved prosthesis in which the sleeve is affixed with the lumen.

FIG. 16 depicts a tubular drainage stent 60 in which the first end 68 of the sleeve 13 is affixed completely within the lumen 12 of the stent 60, the attachment 66 comprising a well-known means such as thermal bonding, adhesive, or a ring of material that can affix the sleeve 13 material to the inner walls 78 of the stent 60. In the illustrative embodiment, the sleeve 13 resides completely within the lumen 12, such that it doesn't not extend beyond the end of the tubular drainage stent 12. This could have particular utility in a urethral stent to prevent migration of pathogenic organism though the stent and into the bladder, while still allowing antegrade flow of urine 17. Having a sleeve 13 extending out of the urethra would normally be less acceptable from a clinical and patient's point of view.

As with each of the embodiments of FIGS. 11–16, it is important that the sleeve be made highly flexible and readily collapsible such that normally exists it a closed state, either by a fluid (air or bodily fluids) applying second pressure in a second direction 18 to at least substantially close the sleeve lumen 15 to greatly reduce retrograde migration of fluids, materials, or pathogens, or merely by the absence of fluid applying a first pressure in a first direction 17. In the preferred embodiments, the sleeve 13 does not maintain its regular tubular configuration (unless perhaps, it is hanging straight down) due to the inability of the thin polymeric material to support such a configuration against gravitational forces. Rather, it collapses into a closed configuration or self-closes to form a one-way valve due to the material adhering to itself, particularly if wet, the atmospheric pressure or fluid pressure in the second direction 18, typically facilitating its closure.

It is to be understood that the above described anti-reflux esophageal, biliary, an urological prostheses 10 are merely illustrative embodiments of this invention. The present invention can also include other devices and methods for manufacturing and using them may be devised by those skilled in the art without departing from the spirit and scope of the invention. It is also to be understood that the invention is directed to embodiments both comprising and consisting of disclosed parts. For example, in the esophageal embodiments, it is contemplated that only a portion of the tubular frame need be coated with the sleeve material. Furthermore, the sleeve material extending from the distal end of the tubular member can be formed with different material from that covering the tubular frame. It is also contemplated that the material of the self-expanding stents can be formed of other materials such as nickel titanium alloys commercially known as nitinol, spring steel, and any other spring-like material formed to assume the flexible self-expanding zig-zag stent configuration.

What is claimed is:

1. A prosthesis for placement in a bile duct, a pancreatic duct, or a urethra of a patient comprising:

a tubular drainage stent sized and configured for placement in a bodily passageway, the tubular drainage stent having a passage extending longitudinally there through, and a sleeve comprising a thin, flexible polymeric material, the sleeve attached about the tubular drainage stent and having a lumen extending longitudinally there through and communicating with the passage of the tubular drainage stent, the sleeve in response to a fluid applying a first pressure in a first direction passing the fluid through the lumen thereof, the sleeve collapsible to at least substantially close the lumen in response to either a fluid applying a second pressure in a second direction or the absence of the fluid applying a first pressure in a first direction;

wherein the tubular drainage stent comprises a non-expanding stent.

2. A prosthesis for placement in a bile duct, a pancreatic duct, or a urethra of a patient comprising:

a tubular drainage stent sized and configured for placement in a bodily passageway, the tubular drainage stent having a passage extending longitudinally there through, and a sleeve comprising a thin, flexible polymeric material, the sleeve attached about the tubular drainage stent and having a lumen extending longitudinally therethrough and communicating with the passage of the tubular drainage stent, the sleeve in response to a fluid applying a first pressure in a first direction passing the fluid through the lumen thereof, the sleeve collapsible to at least substantially close the lumen in response to either a fluid applying a second pressure in a second direction or the absence of the fluid applying a first pressure in a first direction;

wherein the tubular drainage stent comprises a closed tubular conduit.

3. A prosthesis for placement in a bile duct, a pancreatic duct, or a urethra of a patient comprising:

a tubular drainage stent sized and configured for placement in a bodily passageway, the tubular drainage stent having a passage extending longitudinally there through, and a sleeve comprising a thin, flexible polymeric material, the sleeve attached about the tubular drainage stent and having a lumen extending longitudinally therethrough and communicating with the passage of the tubular drainage stent, the sleeve in response to a fluid applying a first pressure in a first direction passing the fluid through the lumen thereof, the sleeve collapsible to at least substantially close the lumen in response to either a fluid applying a second pressure in a second direction or the absence of the fluid applying a first pressure in a first direction;

wherein the tubular drainage stent comprises a closed tubular conduit.

4. A prosthesis for placement in a patient comprising:

a tubular drainage stent having a passage extending longitudinally there through configured to pass only bodily matter;

a retention structure extending from an outer surface of the passage and comprising a flexible material configured to hold the tubular drainage stent within a vessel that conveys fluid without enlarging a diameter of the passage; and a sleeve extending from an end of the tubular drainage stent and having a lumen extending longitudinally there through and communicating with the passage of the tubular drainage stent, the sleeve in response to a fluid applying a first pressure in a first direction passing the fluid through the lumen thereof, the sleeve collapsible to at least substantially close the lumen in response to a fluid applying a second pressure in a second direction;

wherein the tubular drainage stent comprises a non-expandable tubular drainage stent.

5. A prosthesis for placement in a patient comprising:

a tubular drainage stent having a passage extending longitudinally there through configured to pass only bodily matter;

a retention structure extending from an outer surface of the passage and comprising a flexible material configured to hold the tubular drainage stent within a vessel that conveys fluid without enlarging a diameter of the passage; and a sleeve extending from an end of the tubular drainage stent and having a lumen extending longitudinally there through and communicating with the passage of the tubular drainage stent, the sleeve in response to a fluid applying a first pressure in a first direction passing the fluid through the lumen thereof, the sleeve collapsible to at least substantially close the lumen in response to a fluid applying a second pressure in a second direction, wherein the passage comprises an elongate, closed tubular conduit.

* * * * *